(12) United States Patent
Tyagi et al.

(10) Patent No.: US 8,008,478 B2
(45) Date of Patent: Aug. 30, 2011

(54) PROCESS FOR THE PREPARATION OF CEFIXIME

(75) Inventors: Om Dutt Tyagi, Pune (IN); Dnyandeo Ragho Rane, Pune (IN); Sanjay Mahajan, Pune (IN); Yuvraj Atmaram Chavan, Pune (IN)

(73) Assignee: Lupin Limited, Mumbai (IN)

( * ) Notice: Subject to any disclaimer, the term of this patent is extended or adjusted under 35 U.S.C. 154(b) by 769 days.

(21) Appl. No.: 11/722,422

(22) PCT Filed: Dec. 19, 2005

(86) PCT No.: PCT/IN2005/000421
§ 371 (c)(1),
(2), (4) Date: May 22, 2008

(87) PCT Pub. No.: WO2006/067806
PCT Pub. Date: Jun. 29, 2006

(65) Prior Publication Data
US 2009/0227787 A1    Sep. 10, 2009

(30) Foreign Application Priority Data
Dec. 21, 2004    (IN) .................. 1384/MUM/2004

(51) Int. Cl.
*C07D 501/22*    (2006.01)
(52) U.S. Cl. ...................................... 540/222
(58) Field of Classification Search .............. 540/222
See application file for complete search history.

(56) References Cited

U.S. PATENT DOCUMENTS

| | | | |
|---|---|---|---|
| 4,409,214 A | 10/1983 | Takaya et al. | |
| 4,559,334 A | 12/1985 | Takaya et al. | |
| 4,731,443 A * | 3/1988 | Takaya et al. ............ | 540/215 |
| 4,960,889 A * | 10/1990 | Takaya et al. ............ | 544/329 |
| 6,384,212 B1 * | 5/2002 | Yoon et al. ................. | 540/222 |
| 6,800,755 B2 | 10/2004 | Deshpande et al. | |
| 6,825,345 B2 | 11/2004 | Decristoforo et al. | |
| 2004/0082560 A1 * | 4/2004 | Deshpande et al. ....... | 514/200 |
| 2005/0032771 A1 * | 2/2005 | Cabri et al. ................ | 514/202 |
| 2008/0242858 A1 * | 10/2008 | Parthasaradhi et al. .... | 540/222 |

FOREIGN PATENT DOCUMENTS

| | | |
|---|---|---|
| DE | 198 46 449 A1 | 4/1999 |
| DE | 19846 448 A1 | 4/1999 |
| EP | 0 244 637 A1 | 11/1987 |
| GB | 2 330 140 A | 4/1999 |
| GB | 2 330 141 A | 4/1999 |
| WO | WO 95/33753 | 12/1995 |
| WO | WO 99/51607 | 10/1999 |
| WO | WO 99/52913 | 10/1999 |
| WO | WO 2004/037832 A1 | 5/2004 |

OTHER PUBLICATIONS

Yamanaka et al., "Synthesis and Biological Activity of a New Orally Active Cephalosporin, Cefixime (FK027)." *The Journal of Antibiotics* (1986) 1738-1751.

* cited by examiner

*Primary Examiner* — Mark Berch
(74) *Attorney, Agent, or Firm* — Merchant & Gould P.C.

(57) ABSTRACT

The present invention provides an improved process for the preparation of Cefixime of formula (I), a cephalosporine antibiotic with an improved quality in regard to color and solubility. This process includes: (i) reaction of 7-β-(4-chloro-2-alkoxycarbonyl methoxyimino-3-oxobutyromido)-3-cephem-4-carboxylic acid (V) with thiourea at pH 5.0 to 6.0 at temperature 25-40° C. in water, (ii) carbon treatment to the reaction mixture in presence of sodium dithionite or ethylenediaminetetraacetic acid (EDTA) followed by filtration, (iii) acidification of the filtrate obtained in step (ii) to pH 2.0 to 3.0 with acid at 50-80° C. to give cefixime ester (IV) (iv) alkaline hydrolysis of cefixime ester of formula (IV) in water followed by acidification to pH 5.0 to 6.0, (v) precipitation of cefixime (I) by adding ketone solvent followed by acidification to pH 2.0 to 3 and (vi) isolation of solid.

21 Claims, No Drawings

PROCESS FOR THE PREPARATION OF CEFIXIME

FIELD OF INVENTION

The present invention is related to provide an improved process for the preparation of Cefixime of formula (I), a cephalosporine antibiotic with an improved quality in regard to color and solubility.

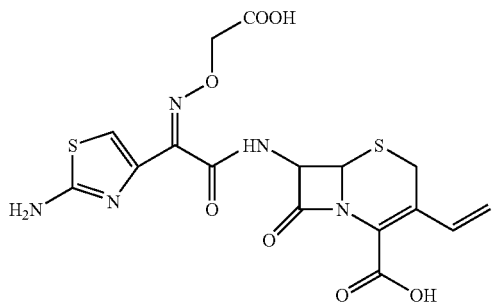

I

BACKGROUND OF THE INVENTION

The present invention relates to an improved process for the preparation of cefixime of formula (I), with an improved quality having better color and solubility. Cefixime (I) is an orally active third-generation cephalosporin antibiotic and is more potent against gram-negative bacteria.

The process for the preparation of the cefixime of formula (I), is disclosed in U.S. Pat. No. 6,825,345 B2 (WO 99/51607) and U.S. Pat. No. 4,409,214 which involves condensation of 7-amino-3-vinyl-3-cephem-4-carboxylic acid (II) with the benzothiazolyl ester of (Z)-2-(2-amino-4-thiazolyl)-(Z)-2-(aryl/alkoxycarbonylmethoxyimino)acetic acid (III, $R_1$ represents ($C_1$-$C_4$) alkyl group or aryl group) to produce ester compound of formula (IV) wherein $R_1$ represents ($C_1$-$C_4$) alkyl group or aryl group and R2 represents hydrogen; followed by hydrolysis to produce cefixime of the formula (I).

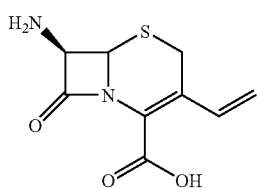

II

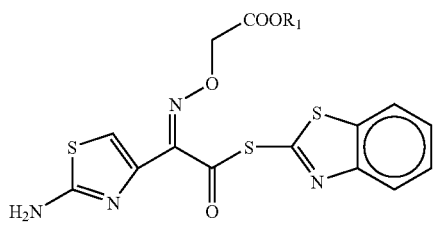

III

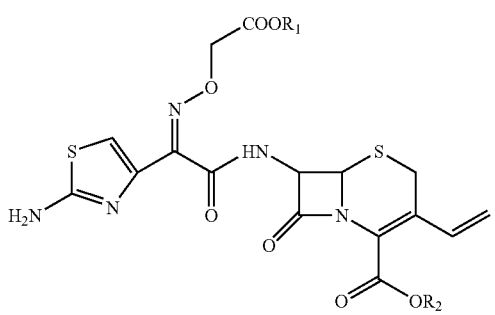

IV

GB 2 330 140 discloses a process for the preparation of cefixime of formula (I) which comprises treating cefixime methyl ester of formula (IV) wherein $R_1$ represents methyl and $R_2$ represents hydrogen with an inorganic base such as $K_2CO_3$ or $Na_2CO_3$ in mixture of dimethylformamide (DMF) and water, which has the following problems: (i) color and quality are poor, (ii) fails in residual solvent (i.e. DMF).

GB 2 330 141 discloses a process for the preparation of the compound of formula (I) which comprises treating cefixime methyl ester of formula (IV) wherein $R_1$ represents methyl and $R_2$ represents hydrogen in an organic solvent such as dichloromethane with aqueous solution of inorganic base such as $K_2CO_3$ or $Na_2CO_3$ and phase transfer catalyst such as quaternary ammonium salts of general formula $R_4N^+X^-$ wherein R is n-butyl, n-pentyl, n-hexyl and X is $Cl^-$, $Br^-I^-$ or $OH^-$. We found that the color, quality and yield of the product obtained from bi-phasic reaction are poor.

The U.S. Pat. No. 4,409,214 and EP 0,763,043 (derived from WO 95/33753) discloses the process for the preparation of cefixime of formula I by hydrolysis of cefixime diester of formula (IV) wherein $R_1$ and $R_2$ both represent tert.butyl, by using hazardous trifluoroacetic acid and anisole.

The PCT application WO 99/052 913 discloses the hydrolysis of cefixime diester of formula (IV) wherein $R_1$ represents tert.butyl and $R_2$ represents naphthylmethyl, by using phenol and protonic acid.

The U.S. Pat. No. 6,800,755 B2 particularly discloses the process of preparation of cefixime of formula I from cefixime ester (IV) wherein $R_1$=$C_1$-$C_4$ alkyl group and $R_2$ represents hydrogen, by hydrolysis with sodium hydroxide in water-water immiscible solvent such as ethyl acetate.

The publication J. Antibiotics (1985), 38, 1738 discloses various processes for the preparation of cefixime of formula (I) and the processes for purification that involve use of column chromatography. The purification by column chromatography cannot be used in large-scale operations, there by making the process commercially not viable.

The steps described in the above publications are more complicated and also suffer from low yield and poor quality.

The inventors have directed their research efforts towards developing a process for the preparation of cefixime which overcome not only the drawbacks of the prior art but which is operationally simple and reproducible on an industrial scale, moreover it gives cefixime trihydrate possessing good quality, colour and solubility profile.

Further the process of present invention avoids use large amounts of solvents for the coupling process as mentioned in the prior-art methods, and thus makes it commercially viable.

OBJECTIVE OF THE INVENTION

The objective of the present invention is to provide an improved process for the preparation of cefixime of the formula (I) in good yield, high purity, having better color and solubility and moreover, that is easy to implement on commercial scales.

SUMMARY OF THE INVENTION

The present invention provides an improved process for the preparation of cefixime of formula (I), which comprises the steps of:

(i) reaction of 7-β-(4-chloro-2-alkoxycarbonyl methoxyimino-3-oxobutyromido)-3-cephem-4-carboxylic acid of formula V wherein $R_1$ represents ($C_1$-$C_4$) alkyl group with thiourea at pH 5.0 to 6.0 at temperature 25-40° C. in water,

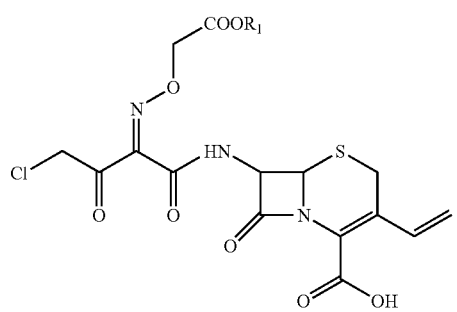

(ii) carbon treatment to the reaction mixture in presence of sodium dithionite or EDTA followed by filtration, (iii) acidification of the filtrate obtained above in step (ii) to pH 2.0 to 3.0 with acid at 60-75° C. to give cefixime ester of formula (I) wherein $R_1$ represents ($C_1$-$C_4$) allyl group and $R_2$ represents hydrogen, (iv) alkaline hydrolysis of cefixime ester of formula (IV) wherein $R_1$ represents ($C_1$-$C_4$) alkyl group and $R_2$ represents hydrogen, in water followed by acidification to pH 5.0 to 6.0, (v) precipitation of cefixime (I) by adding ketonic solvent followed by acidification to pH 2.0 to 2.5 and (vi) isolation of solid.

DETAILED DESCRIPTION

The present invention provides an improved process for the preparation of cefixime of formula (I).

The starting material 7-β-(4-chloro-2-methoxycarbonyl methoxyimino-3-oxobutyromido)-3-cephem-4-carboxylic acid of formula (V) $R_1$ represents ($C_1$-$C_4$) alkyl group was prepared as per synthetic scheme shown below. The compound 4-chloro-2-methoxycarbonyl methoxyimino-3-oxobutyric acid (VI) was converted to acid chloride (VII) with phosphorous pentachloride in dichloromethane followed by treatment with 7β-amino-3-vinyl-3-cephem-4-carboxylic acid (II, 7-AVCA) to give desired intermediate of formula V wherein $R_1$ represents ($C_1$-$C_4$) alkyl group.

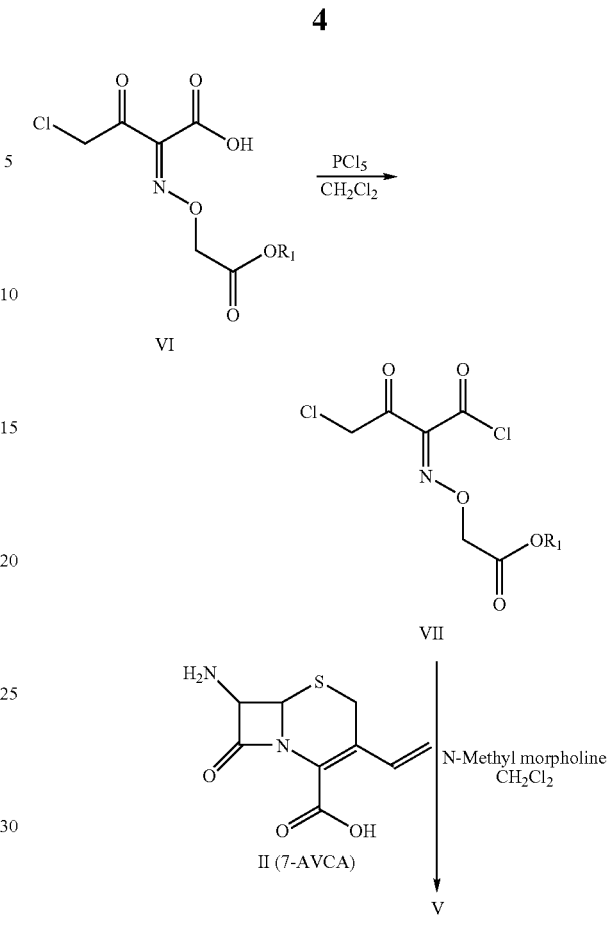

In an embodiment of the present invention $R_1$ represents ($C_1$-$C_4$) alkyl group selected from methyl, ethyl, propyl, isopropyl, n-butyl, t-butyl and sec-butyl group, preferably methyl and $R_2$ represents hydrogen.

The condensation of chloro compound of formula V wherein $R_1$ represents ($C_1$-$C_4$) alkyl group, with thiourea was carried out at pH 5.0 to 6.0, preferably at 5.5 to 5.8. The reaction was performed at temperature 25-40° C., preferably at 3.0-35° C. The reaction was monitored by HPLC and after completion of reaction carbon treatment was carried out in presence of sodium dithionite or ethylenediaminetetraacetic acid (EDTA). Reaction mixture was filtered and filtrate was heated to 50-80° C., preferably at 60-70° C., most preferably to 64-68° C.

The most preferred embodiment of the present invention is the acidification of the filtrate obtained in step (ii) to pH 2.0 to 3.0, preferably to 2.2 to 2.4 with dilute inorganic or organic acid such as aqueous hydrochloric acid at 50-80° C. preferably at 60-70° C., most preferably to 64-68° C. and isolation of solid by filtration at 50-80°, preferably at 60-70° C., most preferably at 64-68° C. The resulting cefixime ester of formula (IV) wherein $R_1$ represents ($C_1$-$C_4$) alkyl group and $R_2$ represents hydrogen, was found to possess better quality and hence on alkaline hydrolysis it led to cefixime trihydrate (I) of high purity, better color and better solubility profile. When the acidification of the filtrate obtained in step (ii) to pH 2.0 to 3.0, preferably to 2.2 to 2.4 and isolation of solid by filtration was done at temperature below 50° C., then the resulting cefixime ester of formula (IV) on alkaline hydrolysis led to cefixime trihydrate (I) having less purity, poor quality in color and poor solubility (see Table 1).

TABLE 1

Dependence of quality of cefixime (I) on the temperature of work up to obtain cefixime methyl ester of formula (IV) wherein $R_1$ represents methyl and $R_2$ represents hydrogen.

| Sr. No. | Temperature of acidification and isolation of cefixime ester (IV, wherein $R_1$ represents methyl and $R_2$ represents hydrogen) | Quality of cefixime (I) | | |
|---|---|---|---|---|
| | | HPLC Purity (%) | Trans-mittance* (%) | Solu-bility# |
| 1 | 65-67° C. | 99.78 | 97.54 | Clear |
| 2 | 65-67° C. | 99.78 | 98.54 | Clear |
| 3 | 45-47° C. | 98.48 | — | Hazy |
| 4 | 45-47° C. | 99.03 | — | Hazy |
| 5 | 25-30° C. | 98.81 | — | Hazy |

*Colour value: 3.3% solution of cefixime (I) prepared in methanol and its colour value checked at 650 nm.
Solubility: 3.3% solution of cefixime (I) prepared in methanol and solubility checked.

The present invention further, provides an improved process for the preparation of cefixime of the formula (I), which avoids the use of hazardous chemicals like trifluoroacetic acid and costly reagents like anisole which are used for deprotection of cefixime ester of formula (IV wherein $R_1$ or $R_2$ or both represents aryl or aralkyl group).

The alkaline hydrolysis of cefixime methyl ester (IV) wherein $R_1$ is methyl and $R_2$ is hydrogen, was carried out by using alkali metal hydroxides such as sodium hydroxide or potassium hydroxide preferably sodium hydroxide. The hydrolysis was performed at temperature 0-30° C., preferably at 0-5° C. After completion of hydrolysis the reaction mixture was acidified to pH 5.0 to 6.0, preferably to 5.5 to 5.8 with dilute solution of inorganic acid such as hydrochloric acid and then subjected to carbon treatment. After filtration the solid was precipitated out from the filtrate by addition of ketonic solvent such as acetone, methyl ethyl ketone preferably acetone. The pH was then adjusted to 2.0 to 3.0, preferably to 2.2 to 2.5 with dilute solution of inorganic acid such as hydrochloric acid.

In another embodiment of the present invention, the cefixime of the formula (I) obtained is in trihydrate form which is a syn isomer.

The process of present invention has the following advantages:
1. operationally simple,
2. reproducible on an industrial scale,
3. it gives cefixime trihydrate possessing very high purity,
4. it gives cefixime trihydrate possessing better colour,
5. it gives cefixime trihydrate possessing better solubility profile,
6. avoids use large amounts of solvents for the coupling process as mentioned in prior art,
7. avoids column chromatographic method for purification which is not plant feasible and
8. commercially viable.

The present invention is exemplified by the following example, which is provided for illustration only and should not be construed to limit the scope of the invention.

EXAMPLE 1

Preparation of [6R-[6α,7β(Z)]]-7-[[(2-amino-4-thiazolyl)[(carboxymethoxy)imino]acetyl]amino]-3-vinyl-3-cephem-4-carboxylic acid (I)

The compound 7β-(4-chloro-2-methoxycarbonyl methoxyimino-3-oxobutyramido)-3-vinyl-3-cephem-4-carboxylic acid (V, R is methyl) (248 g) was added to water (900 ml). Cooled 10° C. The pH was adjusted to 5.7 by adding 10% NaHCO₃ solution (300 ml) slowly at 10-15° C. Thiourea (26.4 g) was added and stirred for 2 hours at 32° C. with maintaining the pH in the range 5.3 to 5.7 with addition of 10% sodium bicarbonate (200 ml). Sodium dithionite (0.9 g) and active carbon (18 g) was added. Stirred for 10 minutes and filtered. The filtrate was heated to 65° C. and acidified to pH 2.2 with 17% HCl (52 ml). Stirred for 30 minutes at 65-68° C. The solid was filtered and washed with hot water (60-65° C.; 900 ml).

The wet solid (cefixime ester of formula IV, wherein $R_1$ represents methyl and $R_2$ represents hydrogen) (180 g) obtained above was added to water (800 ml). Cold solution of sodium hydroxide (24 g) in water (480 ml) was added at 0-2° C. Stirred for 5 minutes at 2-5° C. Acidified to pH 5.1 with 17% HCl (50 ml). Active carbon (12 g) and EDTA (0.9 g) was added, stirred at 5° C. for 30 minutes and filtered. Acetone (800 ml) was added to the clear filtrate. The pH of the solution was adjusted to 2.3 with 17% hydrochloric acid (57 ml) at 34-36° C. The reaction mixture was seeded with pure cefixime (0.2 g) and stirred for 16 hours at 30° C. Cooled to 5° C. and stirred for 3 hours. Solid was filtered, washed with water (480 ml) and dried to give 69.8 g of the title compound (I) of purity 99.76%.

EXAMPLE 2

Preparation of [6R-[6α,7β(Z)]]-7-[[(2-amino-4-thiazolyl)[(carboxymethoxy)imino]acetyl]amino]-3-vinyl-3-cephem-4-carboxylic acid (I)

The compound 7β-(4-chloro-2-methoxycarbonyl methoxyimino-3-oxobutyramido)-3-vinyl-3-cephem-4-carboxylic acid (V wherein R is methyl) (229 g) was added to water (900 ml). Cooled 10° C. The pH was adjusted to 5.7 by adding 10% NaHCO₃ solution (100 ml) slowly at 10° C. Thiourea (26.4 g) was added and stirred for 2 hours at 30° C. with maintaining the pH in the at 5.7 with addition of 10% sodium bicarbonate (160 ml). Sodium dithionite (0.9 g) and active carbon (18 g) was added. Stirred for 30 minutes and then filtered. The filtrate was heated to 65° C. and acidified to pH 2.2 with 17% HCl (50 ml). Stirred for 30 minutes at 65° C. The solid was filtered and washed with hot water (60° C.; 900 ml).

The wet solid (cefixime ester of formula IV, wherein $R_1$ methyl and $R_2$ represents hydrogen) (206 g) obtained above was added to water (800 ml). Cold solution of sodium hydroxide (24 g) in water (480 ml) was added at 0-4° C. Stirred for 5 minutes at 5° C. Acidified to pH 5.0-5.2 with 17% HCl (52 ml). Active carbon (12 g) and EDTA (0.9 g) was added, stirred at 5° C. for 30 minutes and filtered. Acetone (800 ml) was added to the clear filtrate. The pH of the solution was adjusted to 2.3 with 17% hydrochloric acid (20 ml) at 35° C. The reaction mixture was seeded with cefixime trihydrate (0.2 g) and stirred for 16 hours at 25-30° C. Cooled to 5° C. and stirred for 4 hours. Solid was filtered, washed with water (480 ml) and dried to give 69.6 g of the title compound (I). Purity was 99.75%.

The invention claimed is:

1. A process for preparation of cefixime of formula (I)

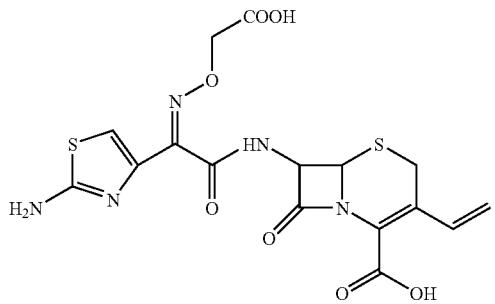

which comprises:

(i) reaction of 7-β-(4-chloro-2-alkoxycarbonyl methoxy-imino-3-oxobutyromido)-3-cephem-4-carboxylic acid of formula V wherein R represents ($C_1$-$C_4$) alkyl group with thiourea at pH 5.0 to 6.0 at temperature 25-40° C. in water,

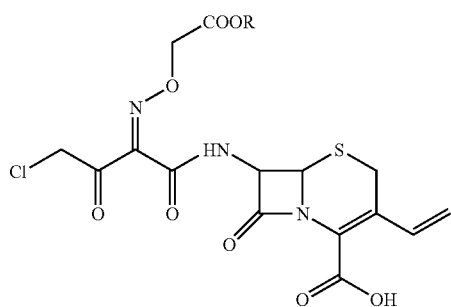

(ii) carbon treatment to the reaction mixture in presence of sodium dithionite or ethylenediaminetetraacetic acid (EDTA) followed by filtration, (iii) acidification of the filtrate obtained above in step (ii) to pH 2.0 to 3.0 with acid at 50-80° C. to give cefixime ester of formula IV wherein $R_1$ represents ($C_1$-$C_4$) alkyl group and $R_2$ represents hydrogen,

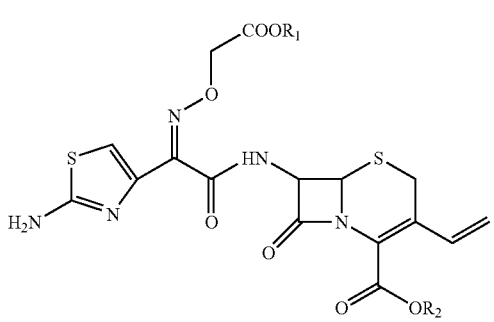

(iv) alkaline hydrolysis of cefixime ester of formula (IV) wherein $R_1$ represents ($C_1$-$C_4$) alkyl group and $R_2$ represents hydrogen obtained above in water followed by acidification to pH 5.0 to 6.0, (v) precipitation of cefixime (I) by adding solvent, the solvent comprising a ketone, followed by acidification to pH 2.0 to 3, and (vi) isolation of solid.

2. A process according to claim 1 wherein, step (i) is carried out at pH 5.5 to 5.8.

3. A process according to claim 1 wherein, step (i) is carried out at 30-35° C.

4. A process according to claim 1 wherein, acidification in step (iii) is carried out to pH 2.2 to 2.4.

5. A process according to claim 1 wherein, acidification in step (iii) is carried out at 60-75° C.

6. A process according to claim 1, further comprising isolating the cefixime ester of formula (IV) wherein $R_1$ represents ($C_1$-$C_4$) alkyl group and $R_2$ represents hydrogen obtained in step (iii), wherein isolating is carried out at 50-80° C.

7. A process according to claim 1 wherein, alkaline hydrolysis in step (iv) is carried out in water by using alkali metal hydroxide.

8. A process according to claim 1 wherein, alkaline hydrolysis in step (iv) is carried out at 0-30° C.

9. A process according to claim 1 wherein, in step (iii) the acidification comprises adding dilute inorganic or organic acid.

10. A process according to claim 1 wherein, in step (v) the precipitation is carried out by adding solvent selected from the group consisting of comprising-acetone and methyl ethyl ketone.

11. A process according to claim 1 wherein, in step (iii) the acidification is carried out to pH 2.0 to 2.5.

12. The process of claim 9, wherein acidification in step (iii) comprises adding HCl, $H_2SO_4$, or acetic acid.

13. The process of claim 12, wherein acidification in step (iii) comprises adding HCl.

14. The process of claim 5, wherein acidification in step (iii) is carried out at 60-70° C.

15. The process of claim 14, wherein acidification in step (iii) is carried out at 64-68° C.

16. The process of claim 6, wherein isolating is carried out at 60-70° C.

17. The process of claim 16, wherein isolating is carried out at 64-68° C.

18. The process of claim 7, wherein the alkali metal hydroxide is selected from the group consisting of sodium hydroxide and potassium hydroxide.

19. The process of claim 18, wherein the alkali metal hydroxide is sodium hydroxide.

20. The process of claim 8, wherein alkaline hydrolysis in step (iv) is carried out at 0-5° C.

21. The process of claim 10, wherein the solvent is acetone.

* * * * *